Figure 1:
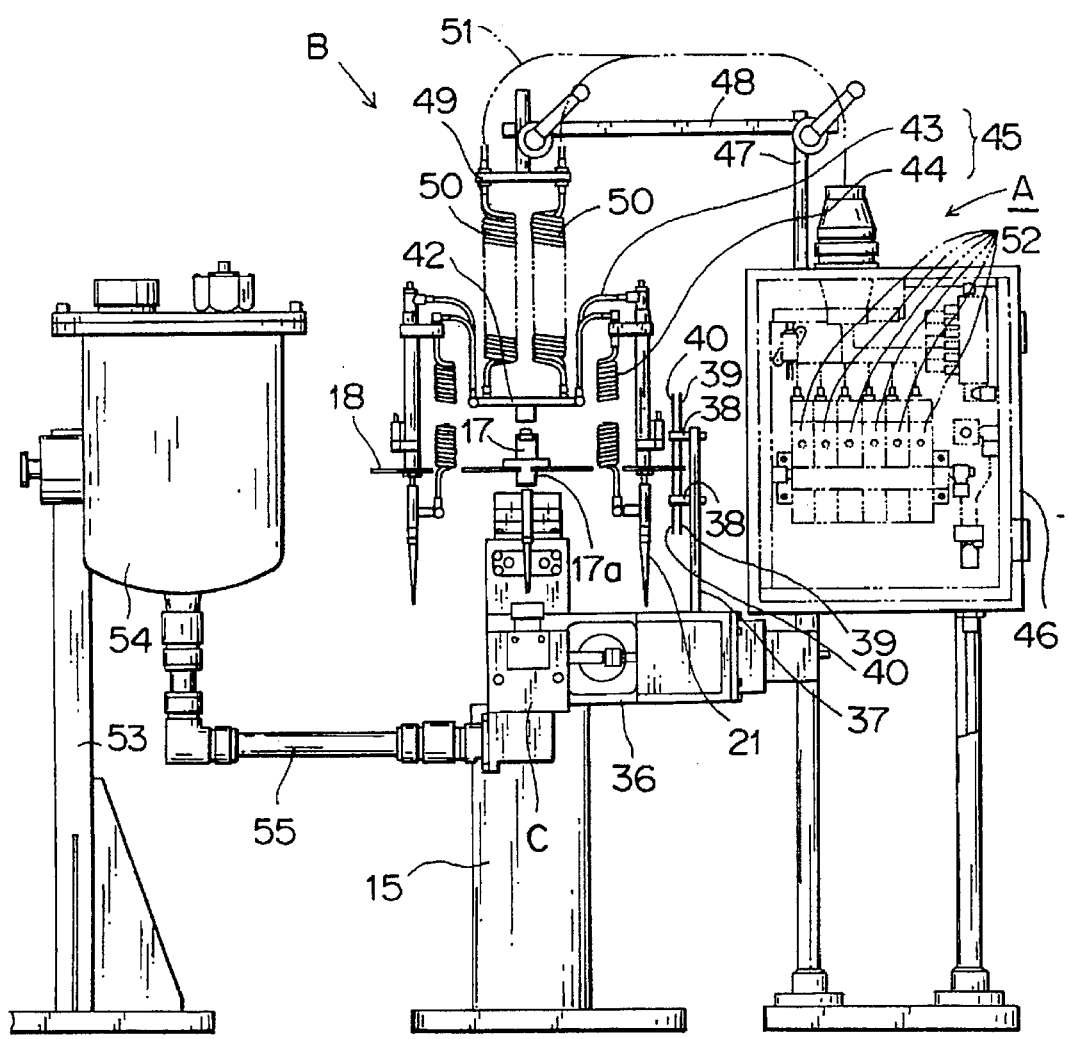

United States Patent [19]
Kohno

[11] Patent Number: 5,660,630
[45] Date of Patent: Aug. 26, 1997

[54] SEEDLIKE SUBSTANCE MAKING APPARATUS

[75] Inventor: Yasushi Kohno, Susono, Japan

[73] Assignee: Yazaki Corporation, Tokyo, Japan

[21] Appl. No.: 415,123

[22] Filed: Mar. 30, 1995

[30] Foreign Application Priority Data

Mar. 31, 1994 [JP] Japan ................... 6-062917

[51] Int. Cl.$^6$ .............. B05C 1/02; C12M 3/00; C12N 11/04
[52] U.S. Cl. ......................... 118/23; 435/286.4
[58] Field of Search ................ 264/4, 4.1, 4.3; 425/5; 435/240.22, 286.4; 118/13, 23, 300

[56] References Cited

U.S. PATENT DOCUMENTS

| | | | |
|---|---|---|---|
| 2,217,336 | 10/1940 | Eden | 264/4 |
| 4,001,480 | 1/1977 | Shank | 435/182 |
| 4,352,883 | 10/1982 | Lim | 435/178 |
| 4,450,877 | 5/1984 | Walker et al. | 264/4 X |
| 4,495,288 | 1/1985 | Jarvis, Jr. et al. | 435/182 X |
| 4,933,122 | 6/1990 | Suzuki et al. | 425/5 X |
| 5,107,787 | 4/1992 | Kouno | 118/23 |
| 5,441,878 | 8/1995 | Thies et al. | 435/240.22 X |
| 5,509,963 | 4/1996 | Kohno | 118/23 |
| 5,512,101 | 4/1996 | Kohno | 118/23 X |

FOREIGN PATENT DOCUMENTS

| | | |
|---|---|---|
| 62-266137 | 11/1987 | Japan . |
| 63-197530 | 8/1988 | Japan . |
| 3-4706 | 1/1991 | Japan . |
| 3-127920 | 5/1991 | Japan . |
| 5-7016 | 2/1993 | Japan . |

*Primary Examiner*—Richard D. Lovering
*Attorney, Agent, or Firm*—Nikaido, Marmelstein, Murray & Oram LLP

[57] ABSTRACT

A seedlike substance making apparatus is provided which overcomes the problems experienced with conventional apparatuses that artificial seeds cannot be dispersed uniformly in a gelling agent, and which makes it possible to arbitrarily set the number of enclosures, such as adventive embryos, and the size of gelled coating. The apparatus comprises a coating material delivery mechanism (C), an enclosure supply mechanism (D) and a tip positioning mechanism (B). The coating material delivery mechanism (C) forms a film of coating material by opening and closing the nozzle plunger (8). The enclosure supply mechanism (D) has a vertically movable supply rod (29) at the bottom of the enclosure container (25) that contains a culture liquid in which the enclosures are immersed. The tip positioning mechanism (B) comprises a rotary plate (18), which is provided with a plurality of air cylinders (19). The piston rod (19a) of each air cylinder (19) is attached with an enclosure suction tip (21), which is connected through a selector valve (52) to the air pressure source (1) and negative pressure source by a pipe.

5 Claims, 11 Drawing Sheets

SEEDLIKE SUBSTANCE MAKING APPARATUS

BACKGROUND OF THE INVENTION

1. Field of the Invention

The present invention relates to a seedlike substance making apparatus which continuously encloses cultured tissues (enclosures) such as adventive embryos into capsules in an aseptic condition.

2. Description of the Prior Art

Among the techniques that disclose the means for making enclosures are Japanese Patent Application Laid-Open Specifications Nos. 62-266137, 63-197530, 3-4706 and 3-127920.

As represented by "the method of making artificial seeds" in Japanese Patent Application Laid-Open Specification No. 3-127920, these techniques disclose a means that disperses and encloses cultured tissues such as adventive embryos into a gelling agent (a material capable of gelling according to chemical reactions), supplies liquid droplets of the cultured tissues through a small hole into a hardener, and sphericalizes the liquid droplets during the process of falling by the application of surface tension. Another means disclosed by these references is to continuously extrude the cultured tissues from a nozzle into a hardener to form them into long string-like shapes and then cut them into appropriate lengths.

The technique of Japanese Patent Application Laid-Open Specification No. 63-197530 moves an end of a hose connected to a sol supply tank in a planetary motion by using a planetary gear to drop sol—which has a number of enclosed tissues dispersed in a coating agent—from the end of the hose into a hardening tank below.

A technique of Japanese Patent Application Laid-Open Specification No. 62-266137 uses a centrifugal force to make the liquid droplets.

Of the means disclosed in the Japanese Patent Application Laid-Open Specification No. 3-127920, the former has a disadvantage that it is difficult to uniformly disperse a number of enclosed tissue elements in a coating agent. The droplets of coating material supplied into the hardening agent include those droplets that contain the enclosed tissue pieces and those that do not. These droplets of coating material are mixed, making it necessary to provide a process for sorting out those coating material droplets containing the enclosures from those that do not.

The extrusion means has a disadvantage in that is extremely difficult to determine the position at which to cut the string-like coating materials into blocks and that therefore, the number of cultured tissue pieces enclosed in the cut coating blocks is variable.

With the techniques of Japanese Patent Application Laid-Open Specifications Nos. 63-197530 and 62-266137, too, it is difficult to uniformly disperse a number of enclosured tissue pieces.

The cultured tissues, the enclosures, are valuable. When the number of enclosures is one, there is no waste. When there are more than one tissue enclosures per encapsulation, the extra tissues may be wasted.

The coating blocks containing no enclosure must be removed by a troublesome selection process.

With these methods, it is not possible to make arbitrary changes to the size of the coating materials and the number of enclosures.

With a seed coating apparatus (Japanese Utility Model Application Laid-Open Specification No. 5-7018) which coats an enclosure with a film of the coating material, it is possible to arbitrarily change the diameter of the encapsulating coating material and the number of enclosures contained therein. To change the capsule diameter, however, requires adjusting by manual operation, the amount of coating material that is delivered. This method, therefore, cannot be applied to an apparatus for making a seedlike substance installed in an aseptic room.

The object of this invention is to solve the above-mentioned problems and to provide an apparatus for making a seedlike substance comprising encapsulated tissue piece(s) enclosed in a coating material, which can insert an arbitrary number of enclosured tissue pieces into a coating block and to enable arbitrary changes to the size of capsule diameter and to the number of enclosures to be made.

SUMMARY OF THE INVENTION

To achieve the above object, the seedlike substance making apparatus of this invention comprises:

a tip positioning mechanism comprising: a rotary drive unit; a rotary plate secured to an output shaft of the rotary drive unit; two or more cylinders mounted on the rotary plate at a plurality of positions, the cylinders each having a rod directed downward; enclosure suction tips provided to lower ends of the cylinder rods, each of the enclosure suction tips being connected with a tube leading through a selector valve to an air pressure source and a negative pressure source; and a position sensor to detect a stop position of the enclosure suction tips;

an enclosure supply mechanism comprising: an enclosure container provided on one side with respect to the output shaft of the rotary drive unit, the enclosure container being open at the top and containing a culture liquid in which enclosures, such as adventive embryos, are immersed. The enclosure container has a through-hole formed at its bottom; a supply rod inserted into the through-hole, having an upper end surface formed with a mounting surface for mounting a portion of the enclosures, and connected at the lower end with a raise/lower actuator; and a water-tight seal to seal a gap between the supply rod and the enclosure container;

a coating material delivery mechanism comprising: a coating material passage provided on a side opposite to the enclosure container with respect to the output shaft to accommodate a coating material; a nozzle plunger inserted into a plunger insertion hole communicating with the coating material passage, the nozzle plunger being adapted to open a valve when the coating material is pressurized; a pressure plunger to pressurize the coating material; and a drive unit to drive the pressure plunger; and a control unit which, according to signals from the position sensor, stops two of the enclosure suction tips directly above the enclosure supply mechanism and the coating material delivery mechanism, actuates a cylinder of the tip positioning mechanism, raises the supply rod, connects the enclosure suction tip directly over the supply rod to a negative pressure, connects the enclosure suction tip directly over the coating material delivery mechanism to an air pressure, and drives the rotary drive unit.

It is preferred that the mounting surface of the supply rod be formed with liquid discharge grooves.

The drive unit of the coating material delivery mechanism can comprise a motor that rotates a specified amount according to commands given by the control unit, a male screw shaft driven by the motor, and a slider connected to the pressure plunger and having a female screw engaged with the male screw shaft.

How the seedlike substance making apparatus of the above construction works is explained below.

The rotary plate rotates together with the output shaft of the rotary drive unit and upon receipt of a signal from the position sensor, stops so that the enclosure suction tips are positioned directly above the nozzle plunger of the coating material delivery mechanism and the supply rod of the enclosure supply mechanism.

Next, the cylinder is activated to lower the enclosure suction tip and the raise/lower actuator of the enclosure supply mechanism is operated to move the supply rod upward, thereby placing on the supply rod a part of the enclosures immersed in the culture liquid in the enclosure container. The culture liquid flows out of the supply rod through the liquid discharge grooves.

The lowered enclosure suction tip comes close to the enclosures on the supply rod and a negative pressure is applied to the enclosure suction tip, which then draws in one of the enclosures.

When the enclosure suction tip takes in the enclosure, the cylinder is actuated to move the enclosure suction tip upward and at the same time the supply rod is lowered into the enclosure container.

In parallel with this enclosure suction operation, the enclosure suction tip that has drawn in the enclosure and is positioned directly above the coating material delivery mechanism is lowered by the operation of the cylinder to come close to the film of the coating material formed beneath the nozzle plunger of the coating material delivery mechanism. Air pressure is supplied into the enclosure suction tip to expel the enclosure onto the film of the coating material.

After simultaneous operation of suction and supply of the enclosure, the rotary drive unit is again operated to rotate the rotary plate through a required amount of angle and the similar operation is repeated.

In the coating material delivery mechanism, the stepping motor of the drive unit rotates a specified angle given by the control unit. The pressure plunger is activated over the length corresponding to this amount of rotation.

The action of the pressure plunger increases the pressure on the coating material in the coating material passage, which in turn causes the nozzle plunger to open the valve, with the result that the coating material flows out from the nozzle plunger in an amount corresponding to the amount of operation of the pressure plunger. After this, the nozzle plunger closes the valve and then a film of the coating material forms in the lower part of the nozzle plunger.

The enclosure suction tip comes close to the film of coating material thus formed; air pressure is supplied to the enclosure suction tip; and the enclosure is deposited onto the film of the coating material.

The film of the coating material droops in a recessed shape by its own weight and encloses the enclosure and air bubbles.

Next, the nozzle plunger again opens the valve to allow the coating material to flow out and enclose the enclosure and bubbles. At the same time, the coating material with added weight is sphericalized by its surface tension while falling into the tank below which contains hardeners.

To increase the coat diameter, the stroke of the pressure plunger needs to be increased by specifying a greater amount of rotation for the motor from the control unit.

In this way, the diameter of the coat or capsule can be adjusted to any arbitrary value without requiring manual operations.

When the number of enclosures is to be changed to two, the enclosure needs to be supplied twice for each valve opening.

The above and other objects, features and advantages of this invention will become apparent from the following description and the appended claims, taken in conjunction with the accompanying drawings in which like parts or elements are denoted like reference characters.

BRIEF DESCRIPTION OF THE DRAWINGS

FIG. 1 is a front view of a seedlike substance making apparatus A;

FIG. 2 is a side view of FIG. 1;

FIG. 3 is a plan view of FIG. 1;

FIG. 4 is a partly cutaway plan view of an essential portion of FIG. 3;

FIG. 5 is a vertical cross section showing an essential portion of a coating material delivery mechanism;

FIG. 6 is a front view of FIG. 5;

FIG. 7 is a partly cutaway front view of a drive section of the coating material delivery mechanism;

FIG. 8 is a horizontal cross section of the drive section of the coating material delivery mechanism;

FIG. 9 is a vertical cross section of an enclosure suction tip;

FIG. 10 is a front view of an essential portion of supply rod;

FIG. 11 is a view as seen from an arrow X in FIG. 10;

FIG. 12 is a perspective view showing a connection between the supply rod and the raise/lower actuator; and FIGS. 13A to 13H are explanatory diagrams showing the process of positioning the enclosure suction tip.

DESCRIPTION OF THE PREFERRED EMBODIMENT

As shown in FIG. 2, the seedlike substance making apparatus A may be divided into a tip positioning mechanism B, a coating material delivery mechanism C, and an enclosure supply mechanism D.

As shown in FIG. 1 and 2, mounted on the wall surface of a stand 15 located at virtually the center of the apparatus is a mount 36, to which the coating material delivery mechanism C is fastened by screws. The tip positioning mechanism B is installed on the top surface of the stand 15.

The coating material delivery mechanism C comprises a valve section C1 shown in FIG. 5 and 6, a drive section C2 shown in FIG. 7 and 8, and a coating material tank 54 installed at the left side of FIG. 1.

The drive section C2, as shown in FIG. 8, comprises slider cases 57, 58, which are joined together to form a slider accommodating chamber 56 therein, and a gear cover 59 fastened to the right end surface of the slider cases 57, 58 by bolts 60.

On the outer surface of the gear cover 59 is secured by bolts 62 a stepping motor 61, whose output shaft 61*a* has a drive gear 63 rigidly mounted on its surface.

The slider case 57 is formed with concentric holes 65. In FIG. 7, the left side hole 64 is fitted with a bearing 66 and the right side hole 65 with a bearing 67. A male screw shaft 68 is rotatably supported by these bearings 66, 67 at a shaft portion 68a formed at its left end and at a shaft portion 68b at its intermediate section.

A flange 68C for receiving thrust is provided at the left end of the shaft portion 68b. A nut 70 is screwed over a male screw portion 69 formed on the right-hand side of the shaft portion 68b. The flange 68C and the nut 70 combine to prevent the male screw shaft 68 from moving in an axial direction.

A shaft portion 71 extending to the right of the male screw portion 69 is fixed with a follower gear 72 in mesh with the drive gear 63.

A nut 73 engaged with the male screw shaft 68 is fitted in a hole formed in a slider 74 that is slidable in the slider accommodating chamber 56.

Figure 7:
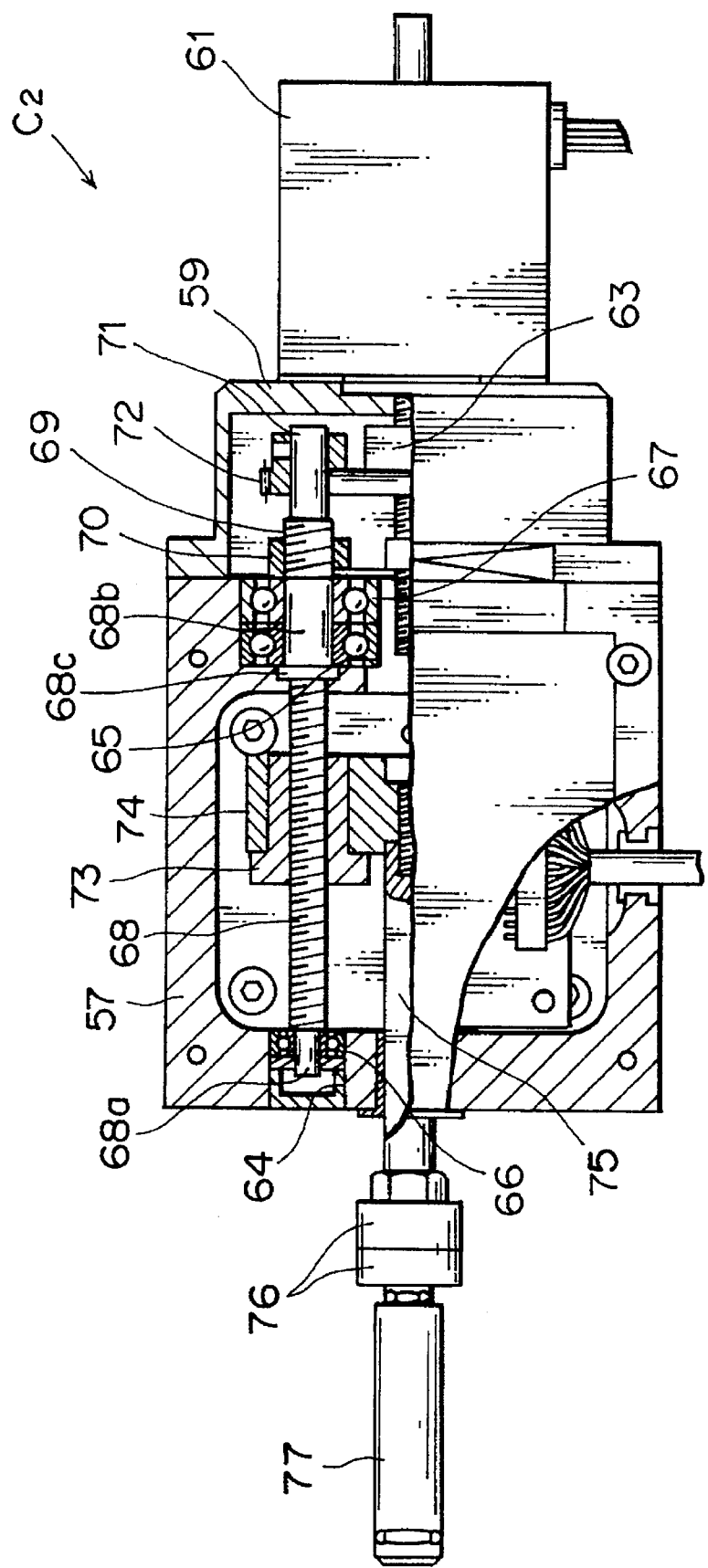

The slider 74 is attached with a slide rod 75 that passes through the slider case 57 and the end of the slide red 75 is fitted with a pressure plunger 77 through a joint 76 (see FIG. 7).

Hence, the rotation of the stepping motor 61 is transmitted through the drive gear 63 and the follower gear 72 to the male screw shaft 68, causing the pressure plunger 77 to move along with the slider 74.

Figure 8:
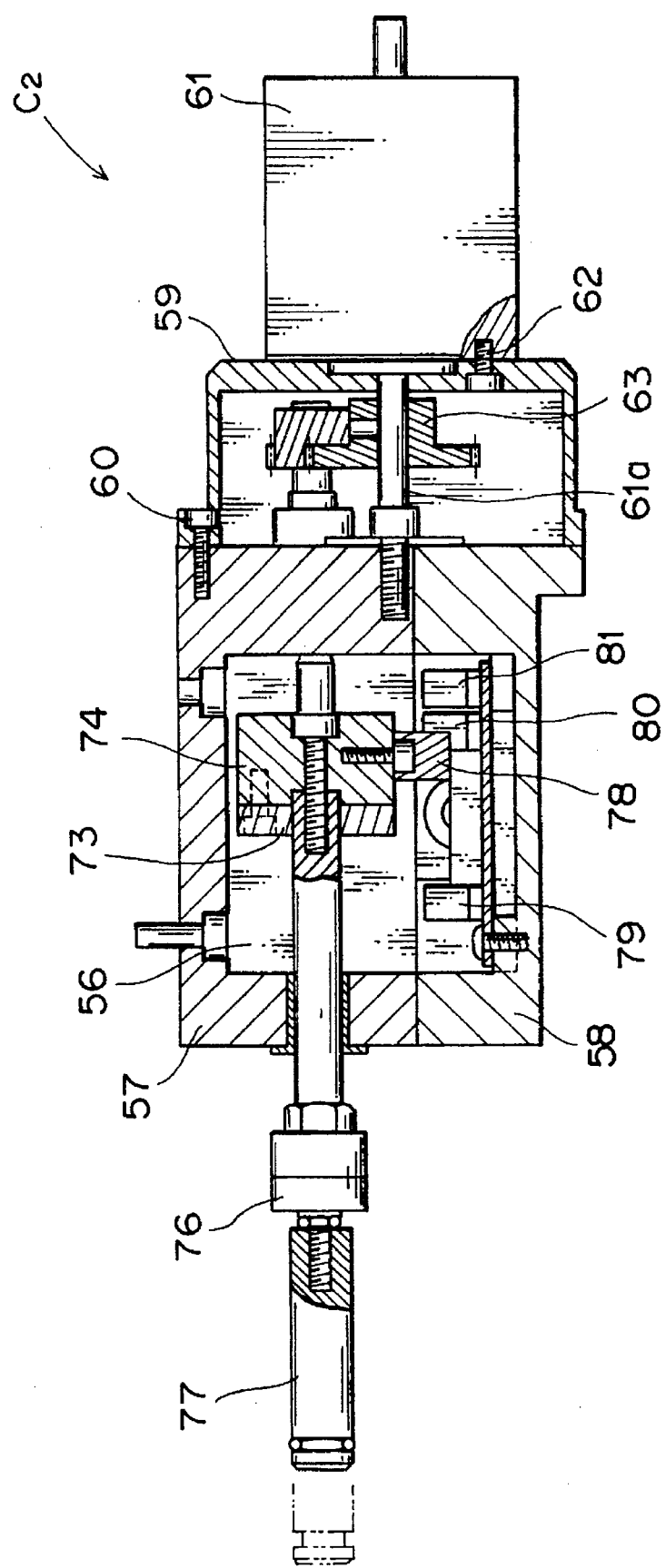
Figure 9:
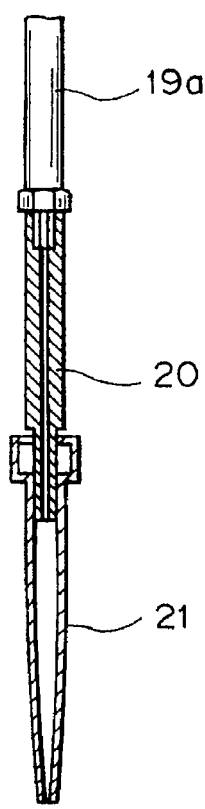

As shown in FIG. 8, the slider 74 is rigidly fitted with a light shielding plate 78. A stroke end sensor 79, an origin reset position sensor 80 and a stroke end sensor 81 are arranged in the direction of movement of the light shielding plate 78. These sensors 79, 80, 81 are of light emission/reception type.

Figure 5:
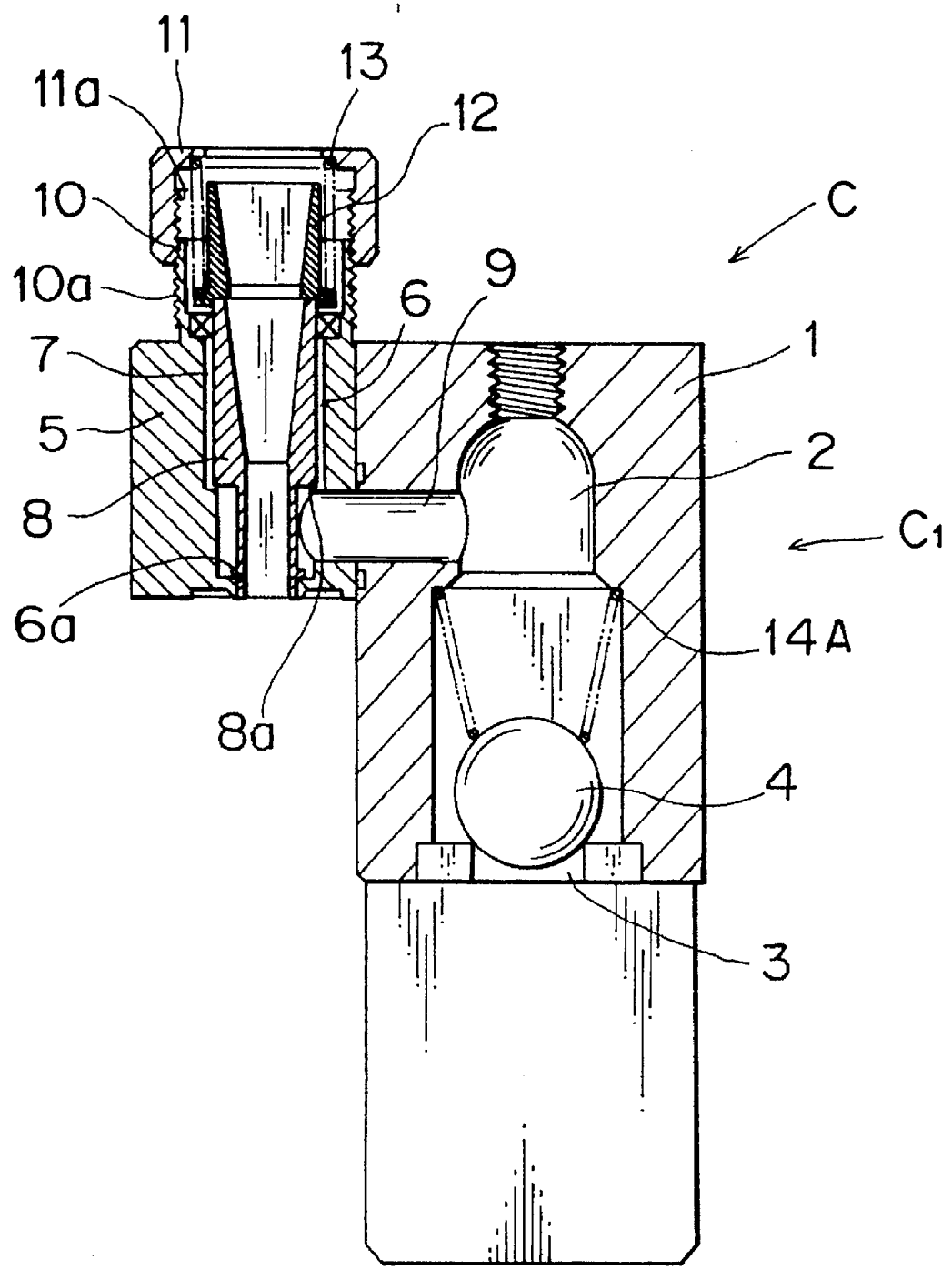
Figure 6:
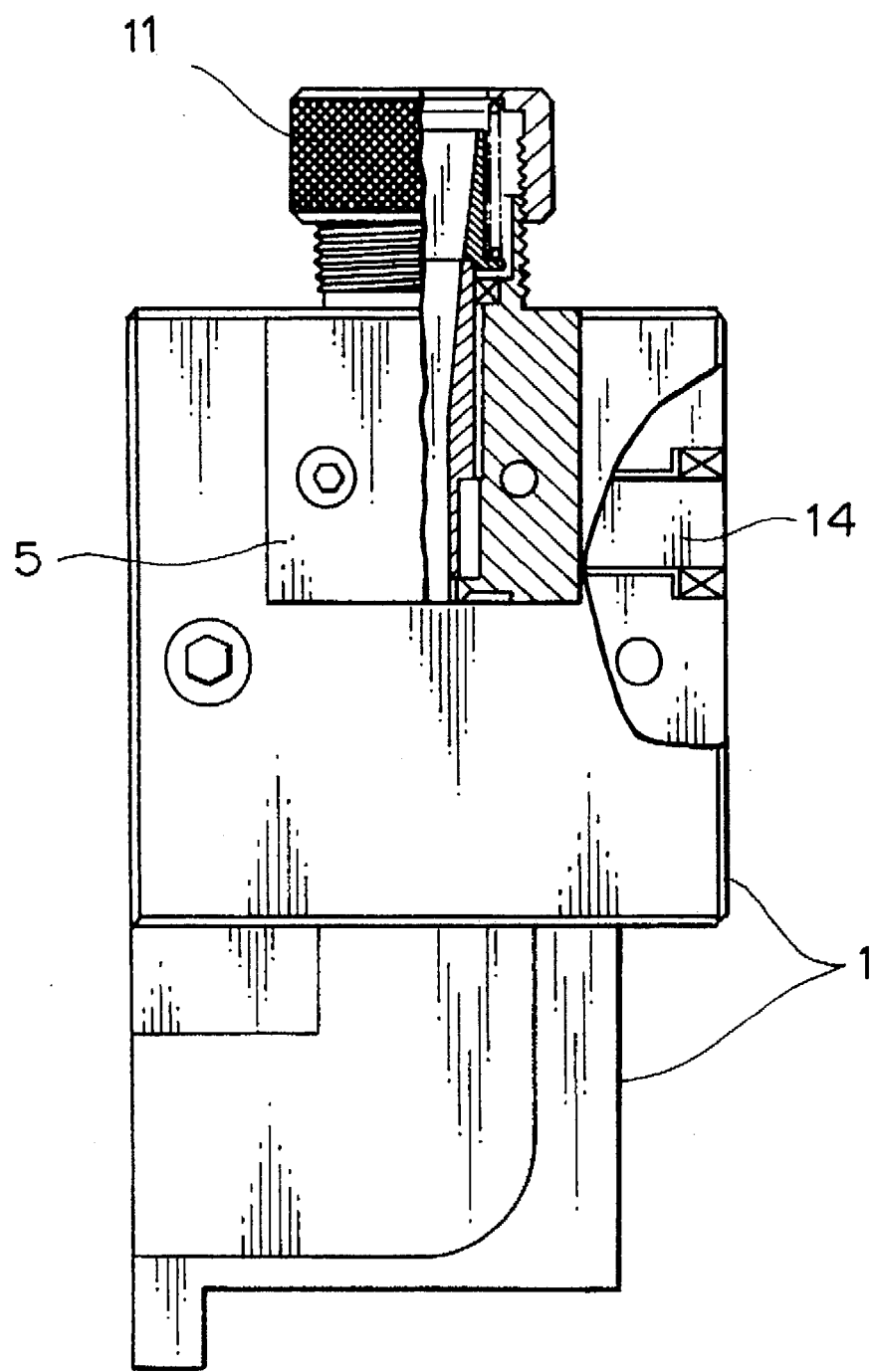

The valve section C1, as shown in FIG. 5 and 6, has a hollow portion 2 in a virtually rectangular parallelepiped valve body 1. The hollow portion 2 opens to the outside through an insertion hole 14, into which the pressure plunger 77 is inserted.

An opening 3 at the lower end surface of the valve body 1 is connected with a pipe passage 55 communicating with the coating material tank 54 (as shown in FIG. 1). Between the opening 3 and the hollow portion 2 is formed a check valve that consists of a steel ball 4 and a spring 14A for pressing the steel ball 4 against the opening 3 to open and close the opening 3. A valve case 5 is mounted at the left hand side of the valve body 1.

The valve case 5 has a valve seat 6a formed at the lower end of a plunger insertion hole 6 that vertically passes through the valve case 5. A bushing 7 is fitted to the inner surface of the plunger insertion hole 6 and a hollow nozzle plunger 8 is inserted vertically movable along the inner surface of the bushing 7.

The outer circumferential surface of the nozzle plunger 8 is smaller in diameter at its lower half than the upper half to form a pressure receiving surface 8a.

A coating material passage 9 connects the plunger insertion hole 6 and the hollow portion 2. The coating material is supplied from the coating material tank through the opening 3 and the check valve to the hollow portion 2 and then charged into the coating material passage 9 and the plunger insertion hole 6.

Provided on the upper surface of the valve case 5 is a cylindrical portion 10 that surrounds the plunger insertion hole 6. The cylindrical portion 10 has a male screw 10a on its outer circumferential surface, over which is fitted a female screw 11a formed on the inner surface of a spring adjuster 11.

On the nozzle plunger 8 is mounted a spring receiver 12, which receives a spring 13 between it and the spring adjuster 11. The lower end portion of the nozzle plunger 8 urged downwardly closes the valve seat 6a. When the coating material pressure plunger protrudes and raises the pressure of the coating material, the pressure receiving surface 8a of the nozzle plunger 8 is pressurized, which in turn causes the nozzle plunger 8 to move upward, opening the valve seat 6a and delivering the coating material.

In FIG. 1, a stay 53 located on the left side is mounted with a coating material tank 54 that accommodates coating material and whose bottom is formed with a hole connected with a coating material transport pipe 55. The end of the coating material transport pipe 55 is connected to the opening 3 of the coating material delivery mechanism C (see FIG. 5).

When the pressure of the coating material in the coating material passage 9 lowers, the coating material in the tank 54 is supplied into the coating material passage 9.

As the nozzle plunger 8 lowers and closes the valve, the delivery of the coating material stops. But the coating material adhering to the underside of the valve seat forms into a film covering the lower part of the plunger insertion hole 6 by its surface tension and droops by its own weight.

In synchronism with this operation, an enclosure is dropped from the enclosure supply mechanism D and enclosed by the coating material film. When the valve is opened, the enclosure falls down together with the supplied coating material and, during the process of fall, forms into a sphericalized shape by the surface tension, before being supplied to the hardening tank (not shown).

Figure 2:
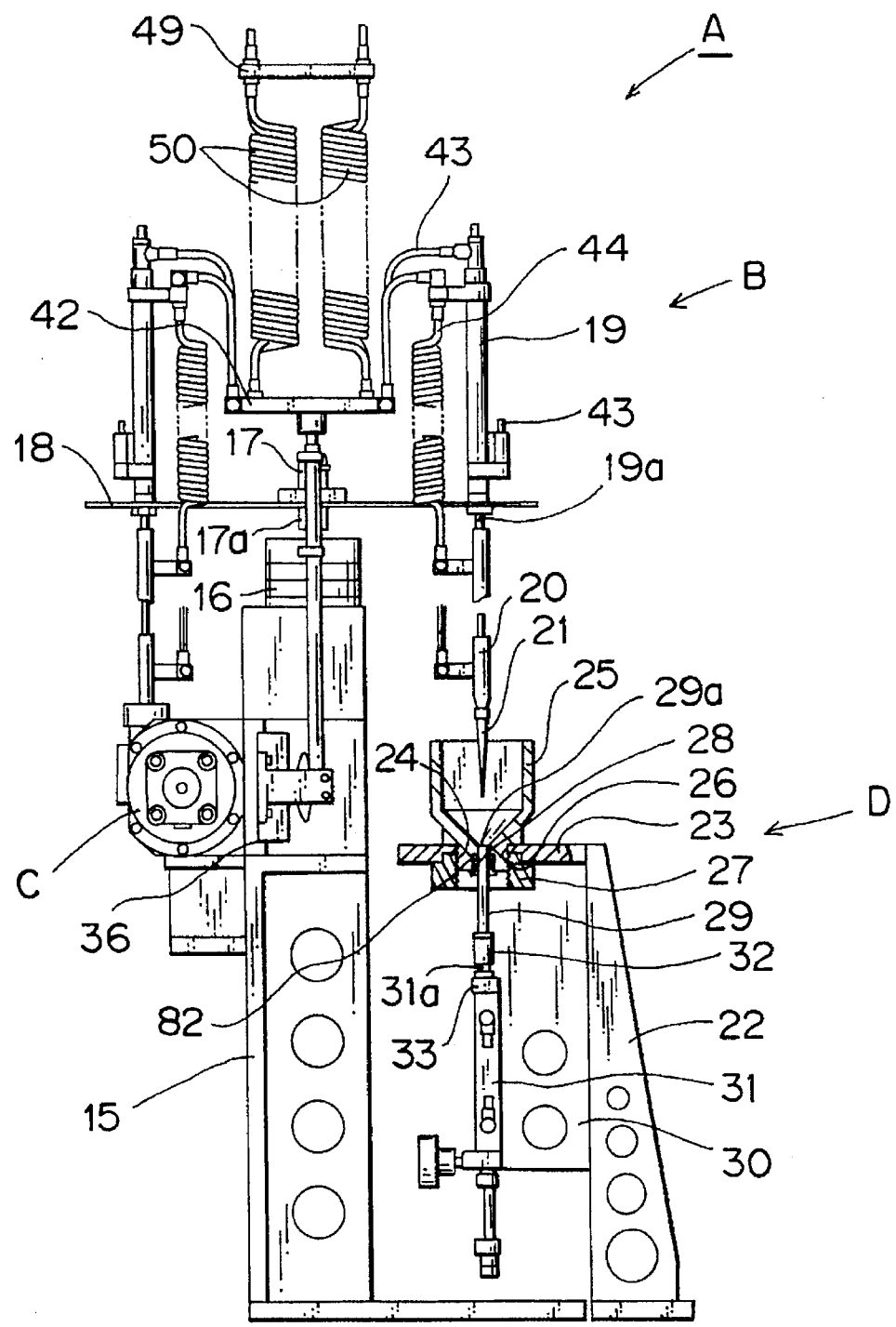
Figure 3:
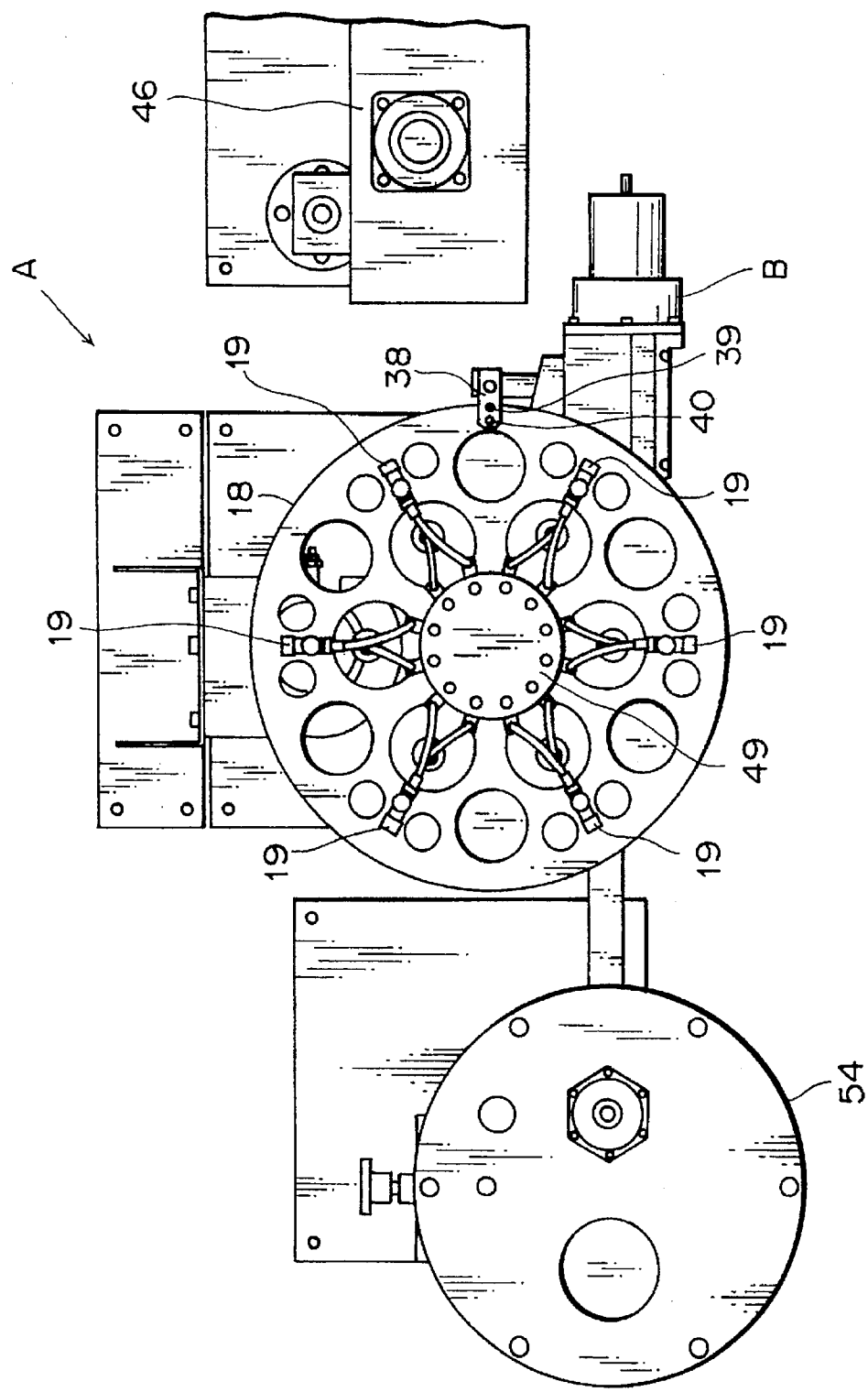

The tip positioning mechanism B, as shown in FIG. 1 and 2, has a rotary drive unit 16 consisting of a stepping motor on the upper surface of the stand 15. The rotary drive unit 16 has an output shaft, which is securely fitted with a support member 17. A rotary plate 18 with a hole in the center is sleeved over a small-diameter portion 17a and fastened to the support member 17 by screws.

The rotary plate 18 is mounted with air cylinders 19—whose piston rods 19a are directed downward—at positions that divide the circumference of the rotary plate 18 into six equal parts. The end of each piston rod 19a is securely connected with a hollow tube 20, whose lower end is attached with an enclosure suction tip 21.

The enclosure suction tip 21 is a cylinder made from a plastic material which is tapered off toward the end. The inner diameter of the end of the suction tip is such that it can draw in a single enclosure. When the kind of enclosure to be processed is changed, the enclosure suction tip 21 is replaced with one having an appropriate diameter for the enclosure.

Because the enclosure suction tip 21 has elasticity, it can easily be attached to or detached from the hollow tube 20.

Figure 4:
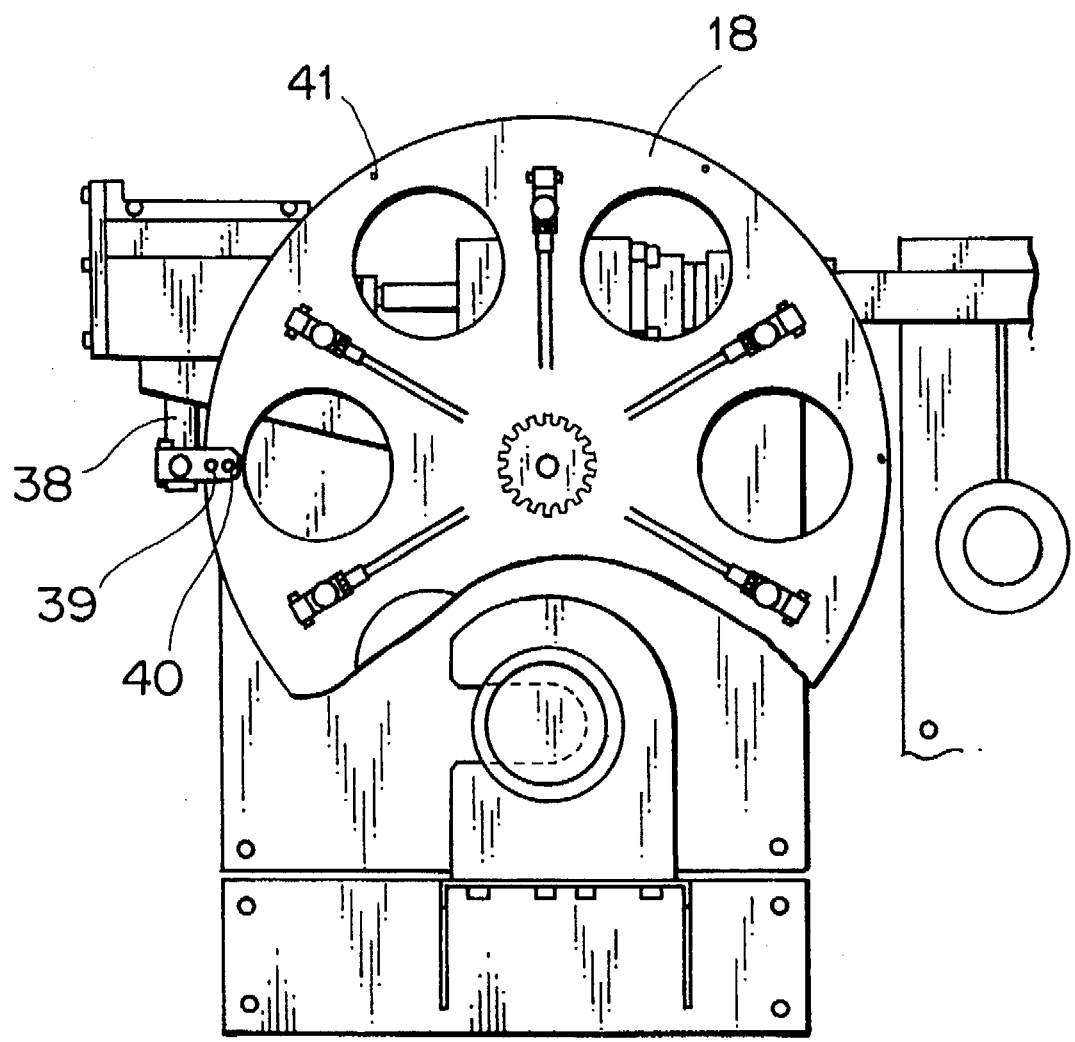

The enclosure supply mechanism D has a bracket 23 mounted on the top of a stay 22, which is installed on a side opposite the coating material delivery mechanism C with respect to the output shaft of the rotary drive unit 16. The bracket 23 has a slot 24 opening to its side, in which a small-diameter portion 26 at the lower part of an enclosure container 25 is movably inserted (see FIG. 2 and 4).

The small-diameter portion 26 has a male screw and the enclosure container 25 is fixed to the bracket 23 by a lock handle 27 having a female screw that engages with the male screw.

The enclosure container 25 opens at the top and contains a culture liquid in which a number of enclosures are immersed. At the bottom, the enclosure container 25 has a through-hole 28 extending through the small-diameter portion 26. In a groove formed in the inner periphery of the small-diameter portion 26 around the through-hole 28 is fitted a water-tight seal 82 that seals the gap between the small-diameter portion 26 and the supply rod 29 inserted vertically movable into the through-hole 28.

In this embodiment, the water-tight seal 82 uses an O-ring.

A raise/lower actuator 31 is mounted on a cylinder stand 30, which is fixed to the side of the stay 22.

Figure 12:
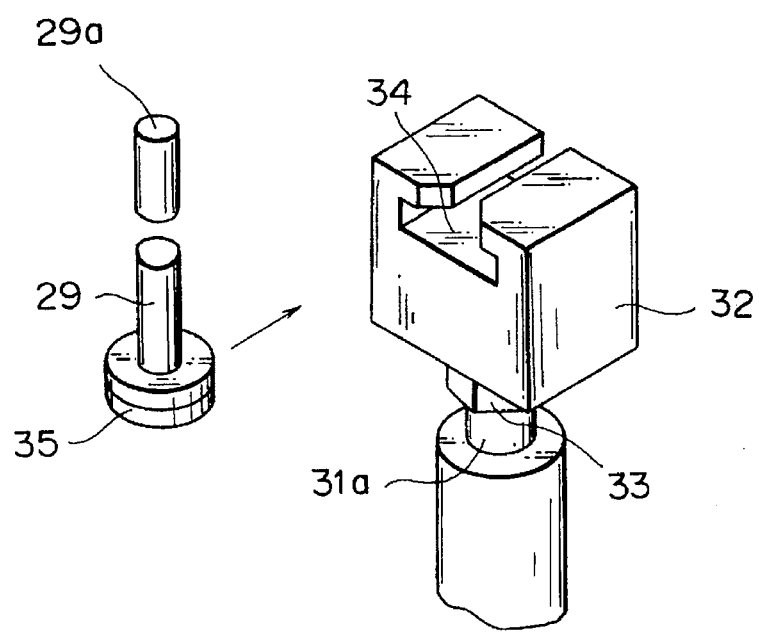

As the raise/lower actuator 31, an air cylinder is used. The upper end of an upwardly acting piston rod 31a is formed with a male screw, with which engage a threaded hole formed at the lower end surface of a joint 32 and a nut 33 that fixes the joint 32 (see FIG. 2 and 12).

The upper surface of the joint 32 is formed with a T-shaped groove 34 extending parallel to the slot 24. The lower end of the supply rod 29 inserted into the through-hole 28 is formed into a T shape in cross section to provide a T-shaped portion 35 that can be removably inserted into the T-shaped groove 34 (see FIG. 12).

Figure 10:
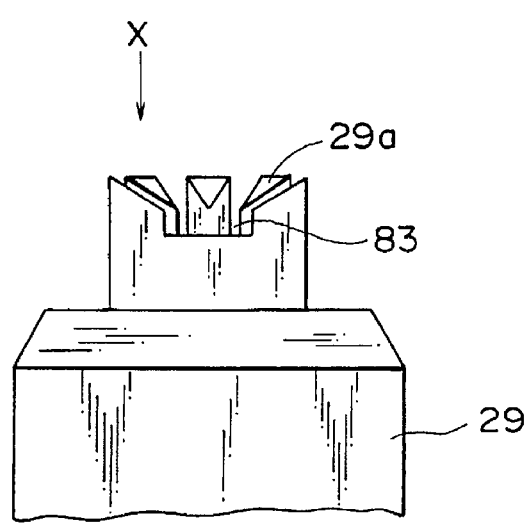
Figure 11:
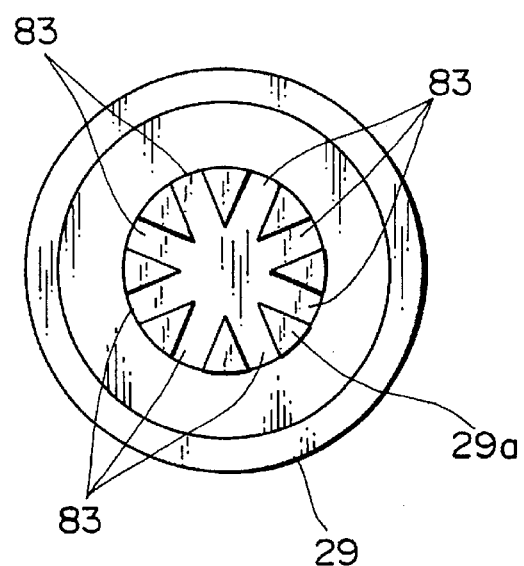

The upper surface of the supply rod 29 is formed with a recessed enclosure mounting surface 29a, which in turn is provided with a plurality of radially extending liquid discharge grooves 83 see FIG. 10 and 11).

A sensor support pillar 37 erected on the mount 36 is securely attaches at two vertically separate locations with arms 38. The arms 38 are each provided with a pair of position sensor 39 and initial position reset sensor 40, having light emitting and receiving portions at top and bottom.

The rotary plate 18 is provided at its outer periphery with positioning small holes 41 that divides the circumference of the rotary plate 18 into six equal parts and one reset timing small hole (not shown).

When the position sensor 39 detects the positioning small holes 41, a rotary plate 18 stop signal is transmitted. When the initial position reset sensor 40 detects the reset timing small hole, an origin reset signal is transmitted.

The upper end of the support member 17 is fixedly fitted with a rotary manifold 42, which has an air pressure tube 43 connected to two vertically separate ports of each air cylinder 19 and a suction tip side tube 45 formed of a tube 44 that supplies an air pressure or negative pressure to the hollow tube 20 (see FIG. 1).

In FIG. 1, a control panel 46, which is installed on the right-hand side and incorporates a control circuit, has a support rod 47, which is securely fitted with a side rod 48 that has a stationary manifold 49 at the end.

The stationary manifold 49 is located above the rotary manifold 42. The rotary manifold 42 and the stationary manifold 49 are connected with ends of elastic tubes 50, which are coiled and slightly deformable.

A stationary side pipe 51 running from the stationary manifold 49 to the control panel 46 communicates through a selector valve 52 in the control panel 46 to an air pressure source and a negative pressure source (not shown) of ejector type that uses air pressure.

Figure 13E:
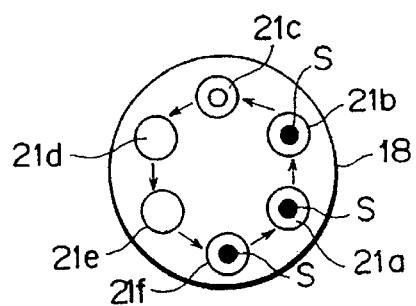
Figure 13A:
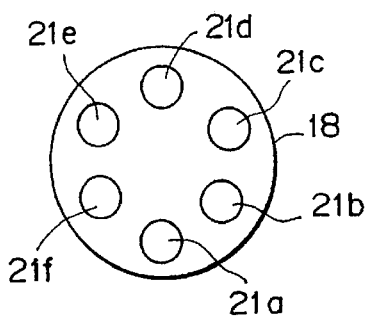
Figure 13F:
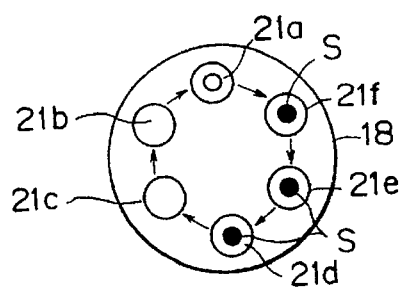

FIGS. 13A through 13H show the procedure of positioning the enclosure suction tip of the enclosure supply mechanism D. In FIG. 13A, it is assumed that the lower side of the rotary plate 18 is an enclosure suction position and the upper side an enclosure supply position, and that the six enclosure suction tips provided to the rotary plate 18 are 21a to 21f. When the rotary plate 18 is at the initial position, the enclosure suction tip 21a is directly above the supply rod 29 of the enclosure container 25 and the enclosure suction tip 21d is immediately above the nozzle plunger 8 of the coating material delivery mechanism C.

When the pressure in the enclosure suction tip 21a becomes negative and an enclosure is drawn in, a negative pressure sensor (not shown) outputs a signal indicating that the negative pressure in the enclosure suction tip 21a has increased, causing the output shaft of the rotary drive unit 16 and the rotary plate 18 to rotate clockwise in FIG. 13A.

Figure 13B:
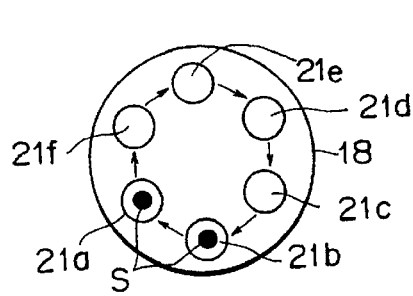

Next, when the position sensor 39 detects the positioning small hole 41 of the rotary plate 18, the rotary drive unit 16 stops and the enclosure suction tip 21b is positioned directly above the supply rod 29 and the enclosure suction tip 21e is positioned above the nozzle plunger 8 (see FIG. 13B).

Next, in the same way, the enclosure suction tip 21b draws in an enclosure (the enclosure drawn in is represented by a symbol S).

Then, the rotary plate 18 rotates 60 degrees clockwise and stops. The enclosure S is drawn into the enclosure suction tip 21c located immediately above the supply rod 29 (see FIG. 13C).

Figure 13G:
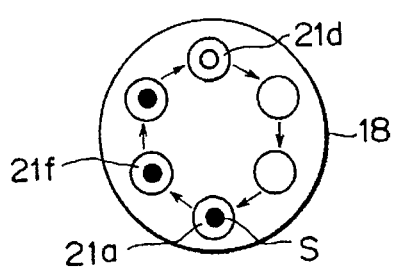
Figure 13C:
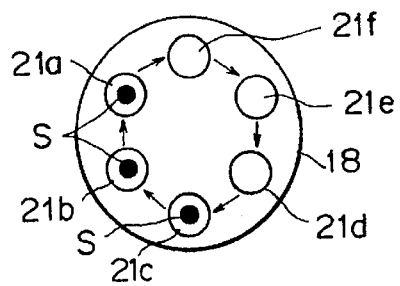
Figure 13H:
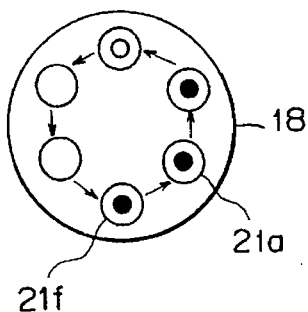
Figure 13D:
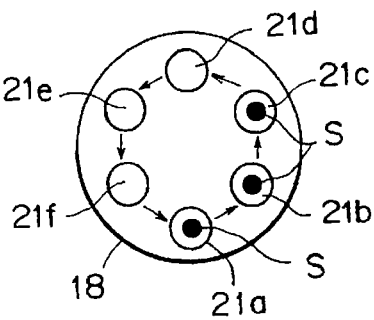

At this time, because the initial position reset sensor 40 detects the reset timing small hole (not shown) of the rotary plate 18, the rotary plate 18 rotates counterclockwise to return to the original position of FIG. 13A (see FIG. 13D).

Thus, the distortion of the elastic tubes 50 is released.

Next, the rotary plate 18 rotates 60 degrees counterclockwise and the enclosure suction tip 21f is positioned directly above the supply rod 29 and sucks the enclosure S in a way similar to the above.

The enclosure suction tip 21a positioned directly above the nozzle plunger 8 is supplied an air pressure to feed the enclosure S onto the film of coating material adhering to the nozzle plunger 8 (see FIG. 13E).

Next, the rotary plate 18 rotates 60 degrees counterclockwise and the enclosure suction tip 21e is located immediately above the supply rod 29 to draw in an enclosure S in a manner similar to that described above.

The enclosure suction tip 21b positioned directly above the nozzle plunger 8 is supplied air pressure to feed the enclosure S onto the film of coating material adhering to the nozzle plunger 8.

Next, the rotary plate 18 rotates 60 degrees counterclockwise and the enclosure suction tip 21d is located immediately above the supply rod 29 to draw in an enclosure S in a way similar to that described above.

The enclosure suction tip 21a positioned directly above the nozzle plunger 8 is supplied air pressure to feed the enclosure S onto the film of coating material adhering to the nozzle plunger 8. (see FIG. 13F).

At this time, the initial position reset sensor 40 detects a reset timing small hole (not shown) of the rotary plate 18; the rotary plate 18 rotates 180 degrees clockwise; the enclosure suction tip 21a is again positioned directly above the supply rod 29 to draw in an enclosure S; and the enclosure in the enclosure suction tip 21d located above the nozzle plunger 8 is fed onto the film of the coating material adhering to the nozzle plunger 8 (see FIG. 13G).

At the same time, distortion of the elastic tubes 50 that were twisted in the opposite direction is released.

Then, the rotary plate 18 rotates counterclockwise to assume the same state as shown in FIG. 13E (see FIG. 13H).

Because the rotation of the rotary plate 18 does not accumulate, the twist of the elastic tubes 50 is limited, preventing an excess force from being applied to the elastic tubes 50, which are coiled so as to be easily deformed.

The overall operation of the seedlike substance making apparatus A with the above construction is explained. When the rotary plate 18 rotates together with the output shaft of the rotary drive unit 16, the position sensor 39 produces a detection signal, causing the rotary drive unit 16 to stop, with the result that the enclosure suction tips 21 are positioned and stopped directly above the nozzle plunger 8 of the coating material delivery mechanism C and the supply rod 29 of the enclosure supply mechanism D.

Next, the air cylinder 19 is activated to lower the enclosure suction tip 21 and at the same time the raise/lower actuator 31 of the enclosure supply mechanism D is operated to raise the supply rod 29 and put on the upwardly moving supply rod 29 a part of the enclosures immersed in the culture liquid in the enclosure container 25. The enclosures on the supply rod 29 comes near the enclosure suction tip 21 while the culture liquid on the supply rod 29 is allowed to flow through the liquid discharge grooves 83 out of the supply rod 29.

The inner pressure of the enclosure suction tip 21 approaching the enclosures becomes negative and one of the enclosures is picked up by the tip by suction. Next, the air cylinder 19 is operated to move the enclosure suction tip 21 upwardly and at the same time the raise/lower actuator 31 is activated to lower the supply rod 29 into the enclosure container 25.

In parallel with this enclosure suction operation, the enclosure suction tip 21 that has drawn in the enclosure and is positioned directly above the coating material delivery mechanism C is lowered by the operation of the air cylinder 19 to come close to the film of the coating material formed in the lower part of the nozzle plunger 8 of the coating material delivery mechanism C. Air pressure is supplied into the enclosure suction tip 21 to supply the enclosure onto the film of the coating material.

After simultaneous operation of suction and supply of the enclosure, the rotary drive unit 16 is again operated to rotate the rotary plate 18 through a required amount of angle and the similar operation is repeated.

In the coating material delivery mechanism C, the stepping motor 61 of the drive section C2 performs forward and reverse rotations alternately by amounts specified by the control unit. The pressure plunger 77 performs a reciprocal motion over the length corresponding to this amount of rotation to move forward and backward the coating material in a sol state in the coating material passage 9 thereby raising and lowering the pressure of the coating material in the passage 9.

When the pressure of the coating material increases, the nozzle plunger 8 opens. When the pressure reduces, the coating material is supplied.

Hence, the amount of the coating material delivered from the nozzle plunger 8 corresponds to the amount of rotation of the stepping motor 61, so that it is possible to easily adjust the amount of the coating material delivered without requiring a manual operation.

When the nozzle plunger 8 closes the valve, the film of the coating material formed in the lower part of the nozzle plunger 8 droops by its own weight. When the enclosure is supplied from the enclosure suction tip 21 and the valve opens, the enclosure and air bubble are enclosed by the coating material, which with added weight falls into the hardening tank.

To increase the coat diameter, the stroke of the pressure plunger needs to be increased by specifying a greater amount of rotation for the motor from the control unit.

When the number of enclosures is to be changed to two, the enclosure needs to be supplied twice for each valve opening.

The kind of enclosure can be changed easily because the enclosure container 25 and the supply rod 29 can be easily removed.

With the above construction, the present invention offers the following advantages.

(1) In the conventional seedlike substance making apparatuses, the coating materials containing the enclosures and those not containing them are mixed and therefore a step is needed to sort out the coating materials containing the enclosures. With the seedlike substance making apparatus of this invention, however, each of the coating materials contains a specified number of enclosures, thereby stabilizing the quality of the products and requiring no sorting work at all.

(2) In the seedlike substance making apparatus of this invention, by giving a command to the control unit from outside an aseptic room, it is possible to change, as desired, the size of coat diameter and the number of enclosures contained in the coat. Because the number of enclosures that are moved close to the enclosure suction tip by the supply rod is small, there is little possibility of the enclosures interfering with each other.

(3) Because the enclosures are immersed in a culture liquid in the enclosure container and because only a small number of enclosures are taken out of the culture liquid by the supply rod during the process of enclosure transfer by suction, the quality of the enclosures can be maintained.

(4) The supply rod is formed with liquid discharge grooves, so that almost no culture liquid is drawn into the enclosure suction tip.

What is claimed is:

1. A seedlike substance making apparatus comprising: a tip positioning mechanism comprising:

a rotary drive unit;

a rotary plate secured to an output shaft of the rotary drive unit;

two or more cylinders mounted on the rotary plate at a plurality of positions, the cylinders each having a rod directed downwardly;

enclosure suction tips provided to lower ends of the cylinder rods, each of the enclosure suction tips being connected with a tube leading through a selector valve to an air pressure source and a negative pressure source; and a position sensor to detect a stop position of the enclosure suction tips;

an enclosure supply mechanism comprising:

an enclosure container provided on one side with respect to the output shaft of the rotary drive unit, the enclosure container being open at the top and containing a culture liquid in which enclosures are immersed, the enclosure container having a through-hole formed at the bottom;

a supply rod inserted into the through-hole, having an upper end surface formed with a mounting surface for mounting a portion of the enclosures, and connected at the lower end with a raise/lower actuator; and a water-tight seal to seal a gap between the supply rod and the enclosure container;

a coating material delivery mechanism comprising:

a coating material passage provided on a side opposite to the enclosure container with respect to the output shaft to accommodate a coating material;

a nozzle plunger inserted into a plunger insertion hole communicating with the coating material passage, the nozzle plunger being adapted to open a valve when the coating material is pressurized;

a pressure plunger to pressurize the coating material; and a drive unit to drive the pressure plunger; and a control unit which, according to signals from the position sensor, stops two of the enclosure suction tips directly above the enclosure supply mechanism and the coating material delivery mechanism, actuates a cylinder of the tip positioning mechanism, raises the supply rod, connects the enclosure suction tip directly over the supply rod to a negative pressure, connects the enclosure suction tip directly over the coating material delivery mechanism to an air pressure, and drives the rotary drive unit.

2. A seedlike substance making apparatus according to claim 1, wherein the mounting surface of the supply rod is formed with liquid discharge grooves.

3. A seedlike substance making apparatus according to claim 1, wherein the drive unit of the coating material delivery mechanism comprises a motor that rotates according to a specified amount given by the control unit, a male screw shaft driven by the motor, and a slider connected to the pressure plunger and having a female screw engaged with the male screw shaft.

4. A seedlike substance making apparatus according to claim 1, wherein six cylinders are mounted on the rotary plate angularly equally spaced by 60 degrees and the rotary plate is correspondingly stepwise rotated by 60 degrees.

5. A seedlike substance making apparatus according to claim 1, wherein the tip positioning mechanism further comprises an initial position reset sensor for rotating and returning the rotary plate to an original position thereof.

* * * * *